United States Patent [19]

Kovacevic

[11] Patent Number: 5,373,730
[45] Date of Patent: Dec. 20, 1994

[54] SKIN COMPLIANCE MEASUREMENT DEVICE

[75] Inventor: Nebojsa Kovacevic, Plymouth, Minn.

[73] Assignee: N.K. Biotechnical Engineering Company, Minneapolis, Minn.

[21] Appl. No.: 980,923

[22] Filed: Nov. 24, 1992

[51] Int. Cl.⁵ .............................................. G01N 3/42
[52] U.S. Cl. ......................................... 73/81; 128/774
[58] Field of Search .................. 73/78, 81, 82, 781, 73/788–791; 128/774, 744

[56] References Cited

U.S. PATENT DOCUMENTS

| | | | |
|---|---|---|---|
| 2,699,671 | 1/1955 | More | 73/81 |
| 4,132,224 | 1/1979 | Randolph | 128/2 |
| 4,151,640 | 7/1979 | Leveque et al. | 128/774 |
| 4,611,487 | 9/1986 | Krenn et al. | 73/81 |
| 5,027,828 | 7/1991 | Kovacevic et al. | 128/774 |

OTHER PUBLICATIONS

Pandux Brochure, Pacific Transducer Corp., Los Angeles, Calif.
Article entitled "Standard Test Method for Rubber Property-Durometer Hardness" from *Annual Book of ASTM Standards*, vol. 09.02.
Article entitled "Instrumentation System for Breast Engorgement Evaluation" by C. D. Ferris.

*Primary Examiner*—Robert Raevis
*Attorney, Agent, or Firm*—Westman, Champlin & Kelly

[57] ABSTRACT

A skin compliance measurement device for measuring the compliance of human skin. The skin compliance measurement device comprises a housing containing two flexible strips attached to the housing at one end and attached to a probe at an opposite end. The probe extends from the flexible strips, through an opening in the bottom of the housing, and contacts an area of skin. A measurement device measures the flexure of the strips when the probe comes into contact with the skin.

16 Claims, 3 Drawing Sheets 5,373,730

SKIN COMPLIANCE MEASUREMENT DEVICE

BACKGROUND OF THE INVENTION

The present invention relates to skin compliance or stiffness and, in particular, to a hand-held device for providing an accurate measurement of the compliance of human skin. Such a device can be useful in many medical and dental situations, such as those where tissues are required to be load bearing or where tissues swell after treatment.

Among the types of devices currently used to measure the compliance of human skin are those using two parallel members rigidly attached to a support at one end, A probe is attached to a free second end of one or both members and contacts the skin, causing the deflection of at least one of the members as it does so. The magnitude of the deflection caused then the probe contacts the skin is measured to determine the compliance of the skin in the area contacted by the probe.

A problem with this type of device is that the magnitude of deflection of the members is continually changing, making it difficult to obtain an accurate determination of skin compliance. In addition, many such devices are overly sensitive to transverse loads at the probe, causing inaccurate readings.

There is therefore a need for a skin compliance measurement device that is capable of eliminating the uncertainty caused by changes in the magnitude of deflection of the members and by transverse loads on the probe. In addition, it would be beneficial if such a device could be adjusted to allow for a more accurate measurement of skin compliance over a variety of compliance value ranges.

SUMMARY OF THE INVENTION

The present invention provides a skin compliance measurement device or sensor for accurately measuring the compliance of human skin. The skin compliance sensor comprises a housing containing two flexible strips, each of which has a first end rigidly attached the housing and a second end rigidly attached to a first spacer block. A probe extends from the first spacer block, through a hollow cylinder inserted in an opening in the bottom of the housing, and contacts a desired area of the skin.

When the probe contacts the skin, the first spacer block is pushed upward, causing the second ends of the flexible strips to bend or flex. This bending is measured by a plurality of strain gages mounted on either side of the flexible strips which send signals indicating the magnitude of the bending to a signal processing circuit.

When the probe is pushed upward far enough, the skin surrounding the probe contacts a bottom side of the hollow cylinder, pushing the cylinder upward and activating a switch mounted on the inside of the housing. The switch sends a signal to the signal processing circuit causing a holding of the signals concurrently sent from the strain gages.

A second spacer block is slidably attached to the first and second flexible strips near their first ends. A threaded bolt extending through a threaded bore in the second spacer block can be rotated for adjustment, causing the second spacer block to slide along a part of the length of the first and second flexible strips.

DETAILED DESCRIPTION OF THE PREFERRED EMBODIMENTS

Figure 1:
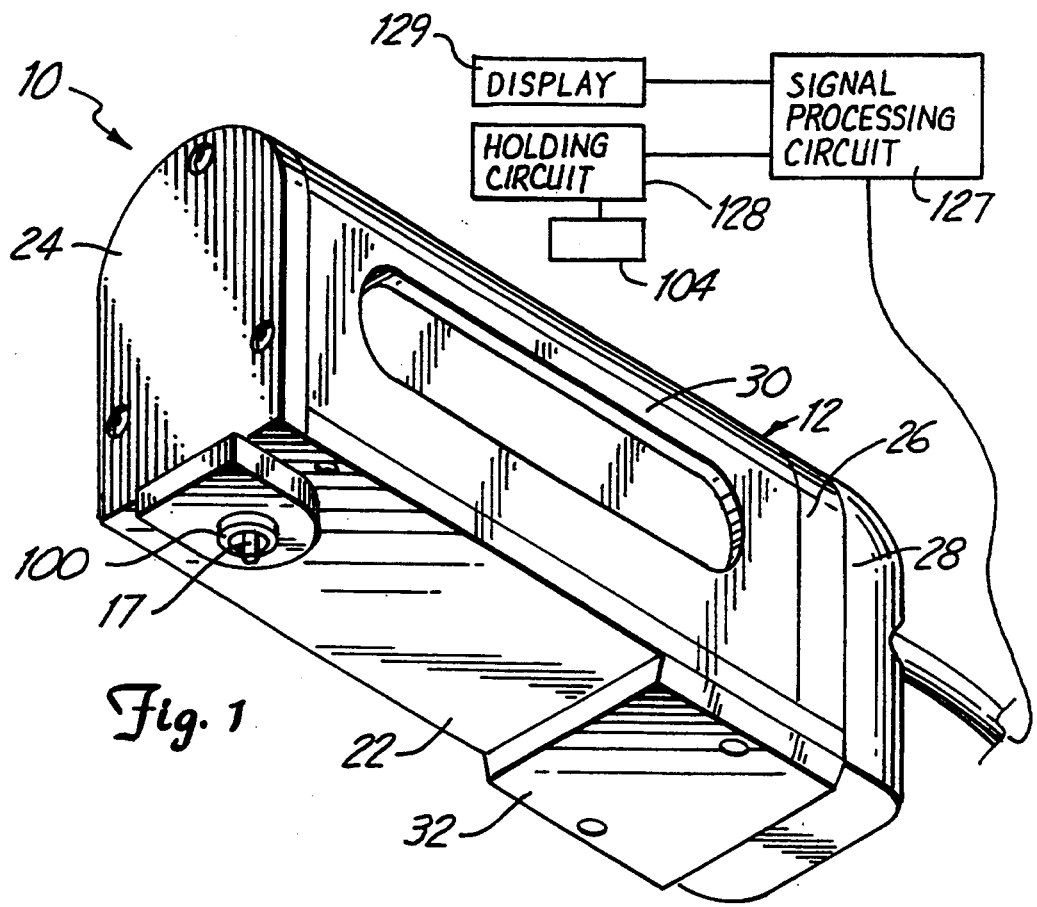
FIG. 1 is a perspective view of a skin compliance measurement device of the present invention.
Figure 2:
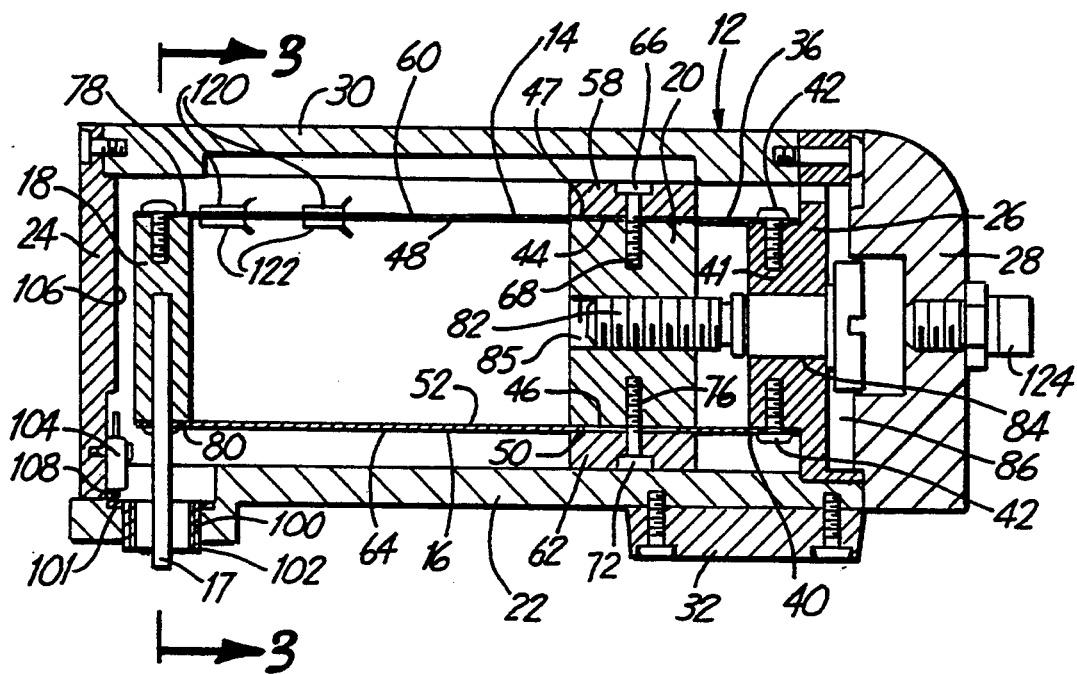
FIG. 2 is a sectional view taken along the line 2—2 of FIG. 1.

A skin compliance sensor 10 of the present invention is shown in FIG. 1. The skin compliance sensor 10, which is shown in more detail in FIG. 2, comprises a housing 12 containing a first flexible strip 14, a second flexible strip 16 and a probe 17. A first spacing block 18 and a movable second spacing block 20 are positioned between the first and second flexible strips 14, 16. The housing 12, which is preferably fabricated from a metal, comprises a base plate 22, a first end cap 24, a second end cap 26, an end cover 28 and a top cover 30 held together by a plurality of screws. A rest pad 32 is attached to a bottom surface of the base plate 22.

Both a first end 36 of the first flexible strip 14 and a first end 40 of the second flexible strip 16 are rigidly attached to an inner portion 41 of the second end cap 26 by two screws 42 and each strict 14, 16 extends through the housing 12 toward the first end cap 24. The first flexible strip 14 has two parallel elongated slots 44 therein near its first end 36 and the second flexible strip 16 has two parallel elongated slots 46 therein near its first end 40.

A first end 47 of the second spacing block 20 contacts a lower side 48 of the first flexible strip 14 and a second end 50 of the second spacing block 20 contacts an upper side 52 of the second flexible strip 16. The second spacing block 20 is held in place between the first and second flexible strips 14, 16 by a first block cap 58 which rests on an upper side 60 of the first flexible strip 14 and a second block cap 62 which contacts a lower side 64 of the second flexible strip 16. The first block cap 58 is held in place by a pair of screws 66, each of which is inserted through a hole in the first block cap 58, through one of the slots 44 in the first flexible strip 14 and into a bore 68 in the first end 47 of the second spacing block 20. The second block cap 62 is held in place through the use of a pair of screws 72, each of which is inserted through a hole in the second block cap 62, through one of the slots 46 in the second flexible strip 16 and into a bore 76 in the second end 50 of the second spacing block 20.

A first end 78 of the first spacing block 18 is rigidly attached to the lower side 48 of the first flexible strip 14 and a second end 80 of the first spacing block 18 is rigidly attached to the upper side 52 of the second flexible strip 16. The first spacing block 18, the second spacing block 20 and the inner portion 41 of the second end cap 26 hold the first and second flexible strips 14, 16 an equal distance from each other throughout their length.

An adjustment screw 82 extends through a hole 84 in the second end cap 26 and a threaded bore 85 in the second spacing block 20. The head of the adjustment screw 82 is located in a recess 86 in the second end cap 26 and can be exposed to a user by removing the end cover 28, which covers the recess 86. When exposed, the adjustment screw 82 can be rotated by a user, causing the second spacing block 20 to slide in either direction along the length of the first and second flexible strips 14, 16.

A hollow cylinder 100 having a circular cross-section and a flange 101 at one end is slidably inserted into a circular opening 102 in the base plate 22. A switch 104 is mounted on a first side 106 of the first end cap 24 and has a pin 108 which extends from a lower side of the switch 104 to a point just above the flange 101. The probe 17, which is rigidly attached to the second end 80 of the first spacing block 18, extends through a hole in the second flexible strip 16 and through the center of the hollow cylinder 100.

A first pair of strain gages 120 are mounted on the upper side 60 of the first flexible strip 14 and a second pair of strain gages 122 are mounted on the lower side 48 of the first flexible strip 14. A plurality of wires electrically connect the strain gages 120, 122 to an electrical connector 124 mounted in the end cover 28. The switch 104 is also electrically connected to the electrical connector 124 by a plurality of wires.

Figure 4:
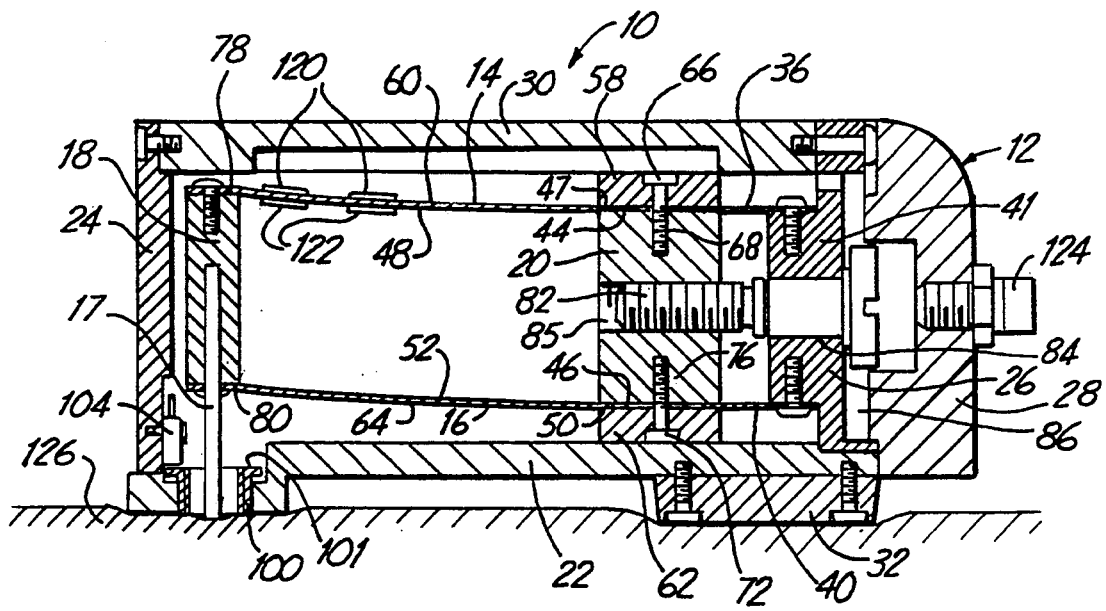
FIG. 4 is a sectional view of the skin compliance measurement device showing the probe coming into contact with human skin.
Figure 5:
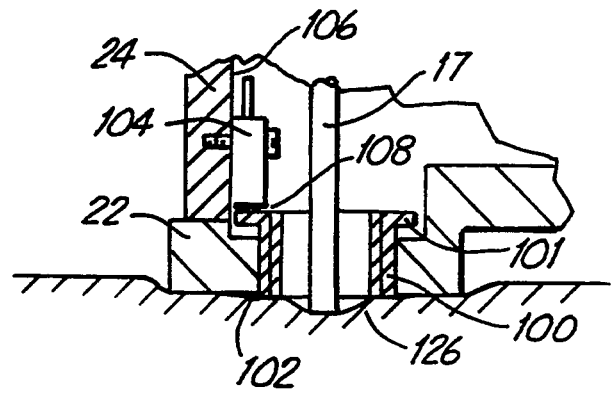
FIG. 5 is a sectional view of a portion of the skin compliance measurement device showing the probe coming into contact with human skin.
Figure 3:
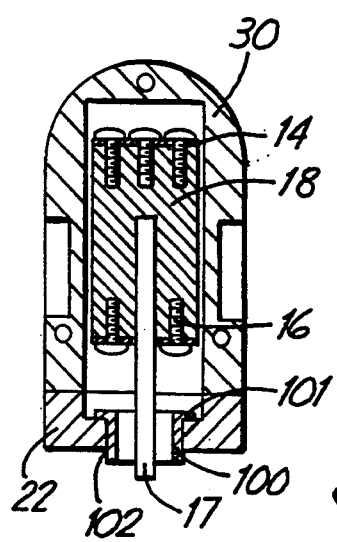
FIG. 3 is a sectional view taken along the line 3—3 of FIG. 2.

The skin compliance sensor 10 is shown coming into contact with an area of skin 126 in FIGS. 4 and 5. When the probe 17 comes into contact with the skin 126, it is pushed upward, causing the first and second flexible strips 14, 16 to flex or bend. The magnitude of this flexure, which corresponds to the magnitude of deflection of the probe 17, is measured and converted into an electrical signal by the strain gages 120, 122 and sent to the electrical connector 124. A signal processing circuit 127 is electrically connected to the electrical connector 124 and provides an output from a strain gage bridge circuit as a skin compliance value based on the signals received from the strain gages 120, 122. The greater the magnitude of flexure of the first and second flexible strips 14, 16, the greater the skin compliance value.

The flexibility of the first and second flexible strips 14, 16 can be decreased by sliding the second spacing block 20 toward the first end cap 24 and can be increased by sliding the second spacing block 20 away from the first end cap 24. This movement of the second block 20, which is limited by the length of the slots 44, 46, permits the flexure of the flexible strips 14, 16 to be more finely differentiated by the strain gages 120, 122, allowing a more accurate measurement of skin compliance in various skin compliance ranges.

When the probe 17 is pushed far enough upward, the skin 126 surrounding the probe 17 comes into contact with the hollow cylinder 100. This causes the cylinder 100 to slide upward within the opening 102 in the base plate 22 and the flange 101 to depress the pin 108. When the pin 108 is depressed, the switch 104 sends an electrical signal to the electrical connector 124, causing a holding circuit 128 electrically connected to both the connector 124 and the signal processing circuit 127 to hold the signals concurrently sent from the strain gages 120, 122. The output provided by the signal processing circuit 127 when the signals sent from the strain gages 120, 122 are held is provided to a display 129 as the skin compliance value.

Figure 6:
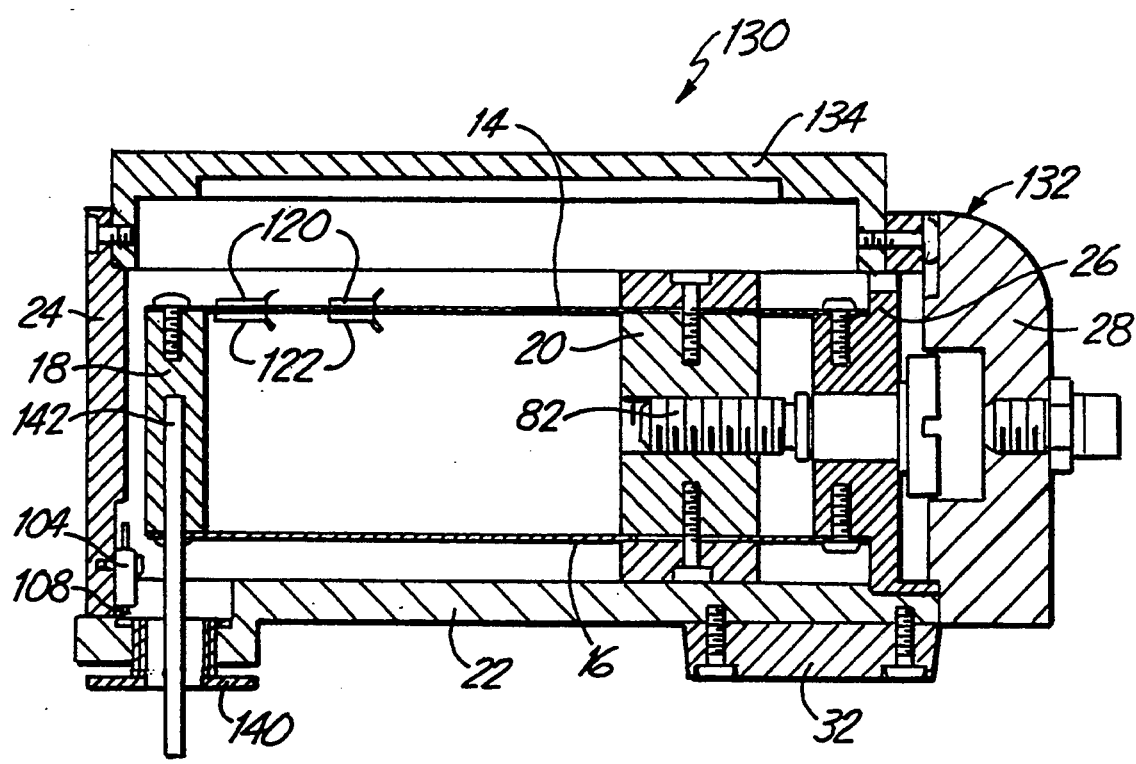
FIG. 6 is a sectional view of a first alternative embodiment of the skin compliance measurement device of the present invention.

In a first alternative embodiment of the present invention, shown in FIG. 6, a skin compliance sensor 130 has substantially the same construction as the skin compliance sensor 10. Among the major differences is the construction of a housing 132 having a top cover 134 which extends farther from the base plate 22 than the top cover 30 in the first embodiment. The higher top cover 134 permits the first flexible strip 14 and the second flexible strip 16 to flex farther within the housing 132 without coming into contact with the top cover 134.

Another major difference between the skin compliance sensor 12 of the first embodiment and the skin compliance sensor 130 is that the skin compliance sensor 130 has a hollow cylinder 140 having a second flange 141 not present on the hollow cylinder 100 in the first embodiment. In addition, the skin compliance sensor 130 has a probe 142 that is longer than the probe 17 in the first embodiment. The combination of a higher top cover 134, second flange 141 and longer probe 142, enables the skin compliance sensor 130 to more accurately measure skin compliance in areas such as the breast where the skin 126 is generally very soft.

The strain gages 120, 122 were described as being mounted on both the lower side 48 and the upper side 60 of the first flexible strip 14. However, the strain gages 120, 122 can be mounted on only one side of the first flexible strip 14 and can be mounted on one or both sides of the second flexible strip 16 as well. In addition, the hollow cylinder 100 can have a variety of shapes and sizes to aid in the measurement of skin compliance in different areas of the body.

Although the present invention has been described with reference to preferred embodiments, workers skilled in the art will recognize that changes may be made in form and detail without departing from the spirit and scope of the invention.

What is claimed is:

1. A skin compliance measurement device for measuring the elastic displacement of tissues, the skin compliance measurement device comprising:
   a housing having an opening therein;
   a first flexible strip contained within the housing;
   a second flexible strip contained within the housing;
   a probe attached to the first and second flexible strips and extending through the opening in the housing for engaging tissues;
   a first sensor for measuring the magnitude of definition of the probe and providing a first signal indicating the magnitude;
   a second sensor for providing a second signal when the second sensor is deflected a predetermined amount, the second signal indicating when the value of the first signal has reached a desired skin compliance value; and
   dampening means for altering the flexibility of the first and second flexible strips.

2. The apparatus of claim 1 wherein the damping means comprises a damping block slidably attached to both the first and second flexible strips. damping block along the length of the first and second flexible strips.

3. The apparatus of claim 2 wherein the means for selectively altering comprises adjustment means extending through the damping block for sliding the damping blocks along the length of the first and second flexible strips.

4. The apparatus of claim 3 wherein the adjustment means comprises a threaded screw.

5. A skin compliance measurement device for measuring the elastic displacement of tissues, the skin compliance measurement device comprising:
- a housing having an opening therein;
- a first flexible strip contained within the housing;
- a second flexible strip contained within the housing;
- a probe attached to the first and second flexible strips and extending through the opening in the housing for engaging tissues;
- a first sensor for measuring the magnitude of deflection of the probe and providing a first signal indicating the magnitude,
- a second sensor for providing a second signal when the second sensor is deflected a predetermined amount, the second signal indicating when the value of the first signal has reached a desired skin compliance value;
- the second sensor comprising a hollow cylinder slidably inserted in the opening in the housing; and
- a switch mounted on an interior surface of the housing, the hollow cylinder being capable of activating the switch when the hollow cylinder is pushed upward a predetermined distance.

6. The apparatus of claim 5 wherein the first flexible strip and the second flexible strip are fabricated from a metal.

7. The apparatus of claim 5 wherein a first end of the first flexible strip and a first end of the second flexible strip are fixedly attached to the housing.

8. The apparatus of claim 7 and a spacer block rigidly attached to both the first flexible strip and the second flexible strip for holding the first and second flexible strips spaced from each other.

9. The apparatus of claim 8 wherein the probe comprises a pin rigidly attached to the spacer block.

10. The apparatus of claim 5 wherein the first sensor comprises a plurality of strain gages.

11. The apparatus of claim 5 and processing mean electrically connected to the first sensor and to the second sensor by a plurality of wires, the processing means being capable of recording and analyzing the signals provided by the first sensor to determine the compliance of the skin contacted by the probe.

12. A skin compliance measuring device for measuring the elastic displacement of tissues, the skin compliance measuring device comprising:
- a housing having an opening therein;
- a probe support mounted within said housing;
- a probe attached to the probe support to permit deflection of the probe from a rest position, wherein the probe extends through the opening in the housing for engaging tissue;
- a sensor for measuring the magnitude of deflection of the probe when the housing is moved toward tissue engaged by the probe and providing a first signal indicating that magnitude;
- a switch mounted within said housing adjacent said probe; and
- a sliding switch actuator extending through the housing adjacent said probe and spaced inwardly from an end of the probe when the probe is in a rest position and as the probe deflects as the housing is moved toward tissue, the sliding member contacts the tissue and actuates the switch to indicate when the first signal should be recorded.

13. The skin compliance measuring device of claim 12 wherein said switch actuator comprises a hollow cylinder slidably inserted in the opening of the housing and surrounding the probe.

14. The skin compliance measuring device of claim 12 wherein said probe support comprises;
- a first flexible strip contained within the housing and having one end anchored relative to the housing;
- a second flexible strip contained within the housing and having one end anchored relative to the housing, the opposite ends of said flexible strips both being connected to the probe and providing a resilient loading of the probe.

15. The skin compliance measuring device of claim 14 and dampening means for selectively altering the flexibility of the first and second flexible strips.

16. A skin compliance measuring device comprising:
- a frame having a base plate with an opening in the base plate;
- a skin compliance measuring probe extending through the opening;
- load sensitive means for mounting the probe relative to the base plate on a first side of the base plate with the probe extending through the opening to a second opposite side of the base plate such that the probe can contact tissue and deflect when the base plate is moved toward such tissue;
- slidable means extending through said base plate and adapted to engage the tissue when the probe has deflected a predetermined amount; and
- switch means operatively associated with said slidable means and actuated when a portion of said slidable means engaging the tissue moves relative to the base plate a preselected amount, to provide a signal indicating that the probe has deflected to a point where skin compliance measurements should be recorded.

* * * * *

UNITED STATES PATENT AND TRADEMARK OFFICE
CERTIFICATE OF CORRECTION

PATENT NO. : 5,373,730
DATED : December 20, 1994
INVENTOR(S) : Nebojsa Kovacevic It is certified that error appears in the above-indentified patent and that said Letters Patent is hereby corrected as shown below:

Title page, item [56]

Cancel [4,151,640] and insert --4,159,640.

Column 4, line 48, cancel [definition] and insert --deflection--.

Signed and Sealed this

Twenty-fifth Day of July, 1995

*Attest:*

BRUCE LEHMAN

*Attesting Officer*   *Commissioner of Patents and Trademarks*